(12) United States Patent
Secrist, III et al.

(10) Patent No.: US 7,148,223 B2
(45) Date of Patent: *Dec. 12, 2006

(54) 4'-THIO-L-XYLO FURANOSYL NUCLEOSIDES, PRECURSORS THEREOF, PREPARATION AND USE THEREOF

(75) Inventors: John A. Secrist, III, Birmingham, AL (US); Kamal N. Tiwari, Birmingham, AL (US); John A. Montgomery, Birmingham, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/045,085

(22) Filed: Jan. 31, 2005

(65) Prior Publication Data

US 2005/0130969 A1 Jun. 16, 2005

Related U.S. Application Data

(60) Division of application No. 10/237,192, filed on Sep. 9, 2002, now Pat. No. 6,914,061, which is a continuation of application No. PCT/US01/07323, filed on Mar. 8, 2001.

(60) Provisional application No. 60/187,867, filed on Mar. 8, 2000.

(51) Int. Cl.
*A61K 31/54* (2006.01)
*C07D 265/38* (2006.01)

(52) U.S. Cl. ............... 514/249; 514/323; 514/329; 514/616; 536/4.1; 536/17.2; 536/17.3; 536/18.5; 536/27.1; 536/27.2; 536/27.6; 536/27.7; 544/264; 544/350; 549/13

(58) Field of Classification Search ................ 514/249, 514/323, 329, 616; 536/4.1, 17.2, 17.3, 18.5, 536/27.1, 27.2, 27.6, 27.7, 27.81, 26.8; 544/264, 544/350; 549/13; 436/17.2
See application file for complete search history.

(56) References Cited

U.S. PATENT DOCUMENTS 6,252,061 B1 6/2001 Sampath et al.

OTHER PUBLICATIONS

"Synthesis and biological activity of certain 4'-thio-D-arabinofuranosylpurine nucleosides." by Secrist III et al., J. Med. Chem. 41. pp. 3865-3871, 1988.

*Primary Examiner*—Shaojia Anna Jiang
*Assistant Examiner*—Devesh Khare
(74) *Attorney, Agent, or Firm*—Connolly, Bove, Lodge & Hutz, LLP

(57) ABSTRACT

Compounds represented by the formula 1:

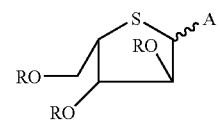

(1)

A is selected from the group consisting of

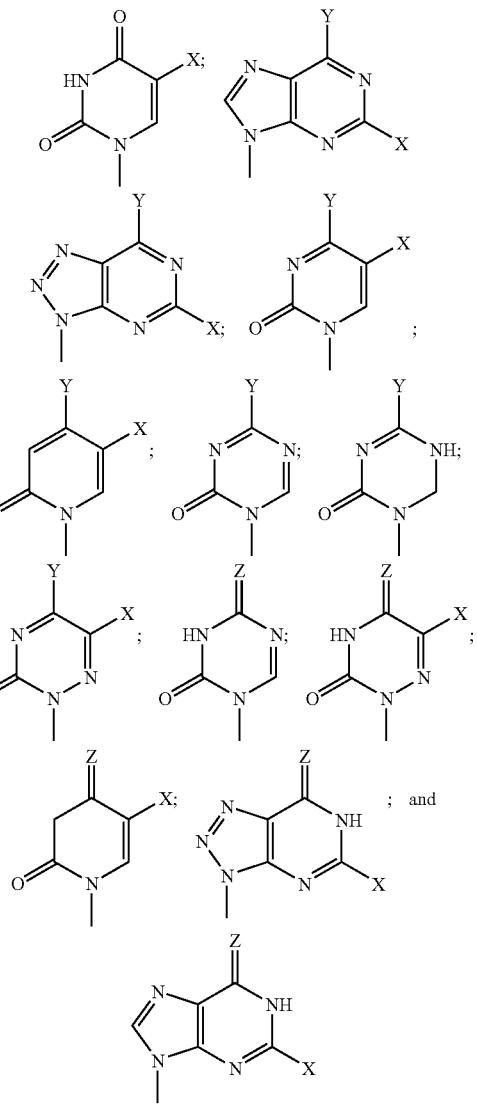

wherein each R individually is H or acyl, Y is X, $N_3$, $NH_2$, monoalkylamino, or dialkylamino; Z is O or S; and
X is selected from the group consisting of hydrogen, halo, hydroxy, alkoxy, alkyl, haloalkyl, alkenyl, haloalkenyl, alkynyl, amino, monoalkylamino, dialkylamino, thioaryl, thioalkyl, allylamino, cyano and nitro; tautomers thereof; and pharmaceutically acceptable salts thereof are provided along with methods for their fabrication. Various of these compounds can be used as anticancer agents, or antiviral agents or to inhibit DNA replication.

28 Claims, No Drawings

U.S. PATENT DOCUMENTS 6,596,858 B1    7/2003   Sampath et al.

6,914,061 B1 *  7/2005   Secrist et al. ............... 514/249

OTHER PUBLICATIONS

"Synthesis of (−(4-thioxylofuranosyl) adenine via a novel glycosylation reaction." by Hartsel et al., Tetrahedron Letters, 39, pp. 205-208, 1998.

* cited by examiner

4'-THIO-L-XYLO FURANOSYL NUCLEOSIDES, PRECURSORS THEREOF, PREPARATION AND USE THEREOF

CROSS-REFERENCE TO RELATED APPLICATIONS

This application is a division of U.S. patent application Ser. No. 10/237,192 filed Sep. 9, 2002, now U.S Pat. No. 6,914,061 which was a continuation of International Application No. PCT/US01/07323 filed Mar. 8, 2001, which claimed priority from U.S. Provisional Patent Application Ser. No. 60/187,867 filed Mar. 8, 2000.

FEDERALLY SPONSORED RESEARCH AND DEVELOPMENT

This invention was supported by Grant CA-34200 from National Institutes of Health.

TECHNICAL FIELD

The present invention relates to new 4'-thio-L-xylofuranosyl nucleosides and precursors thereof. Compounds employed according to the present invention have exhibited good anticancer activity and good antiviral activity. The present invention is concerned with treating patients in need of an antiviral agent by administering to the patient certain 4'-thio-L-xylofuranosyl compounds. The present invention also relates to a new process for preparing the compounds employed according to the present invention.

BACKGROUND OF INVENTION

A large amount of research has been conducted over the years related to developing treatments against cancer and viral diseases. Some of this research has been successful in finding clinically approved treatments. Nevertheless, efforts continue at an ever-increasing rate in view of the extreme difficulty in uncovering promising antiviral and anticancer treatments. For example, even when a compound is found to have antiviral or anticancer activity, there is no predictability of it being selective in humans against virus or cancer cells.

Of the DNA viruses, those of the Herpes group are the source of the most common viral illnesses in man the group includes herpes simplex virus (HSV), varicella zoster virus (VZV), and cytomegalovirus (CMV). Most of these viruses are able to persist in the host cells; once infected, individuals are at risk of recurrent clinical manifestations of infection, which can be both physically and psychologically disabling. Infections with human cytomegalovirus (HCMV) are apparently ubiquitous in the general population. The virus may produce an acute disseminated infection in neonates and such generalized infection is often fatal. Congenital infections in children with HCMV may result in neurological damage and may later result in severe auditory defects and mental retardation. While infection is usually asymptomatic in normal adult individuals, primary HCMV infection or reactivation of latent HCMV invention can cause serious, life threatening disease in immunosuppressed patients.

SUMMARY OF INVENTION

It has been found according to the present invention that certain thioxylofuranosyl cytosine compounds are suitable as anticancer agents and antiviral agents.

More particularly, the present invention relates to compounds represented by the formula 1:

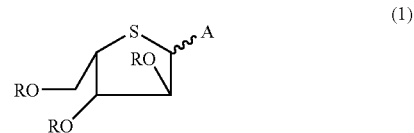

wherein each R individually is H, an alkyl group, or an acyl group;

A is selected from the group consisting of

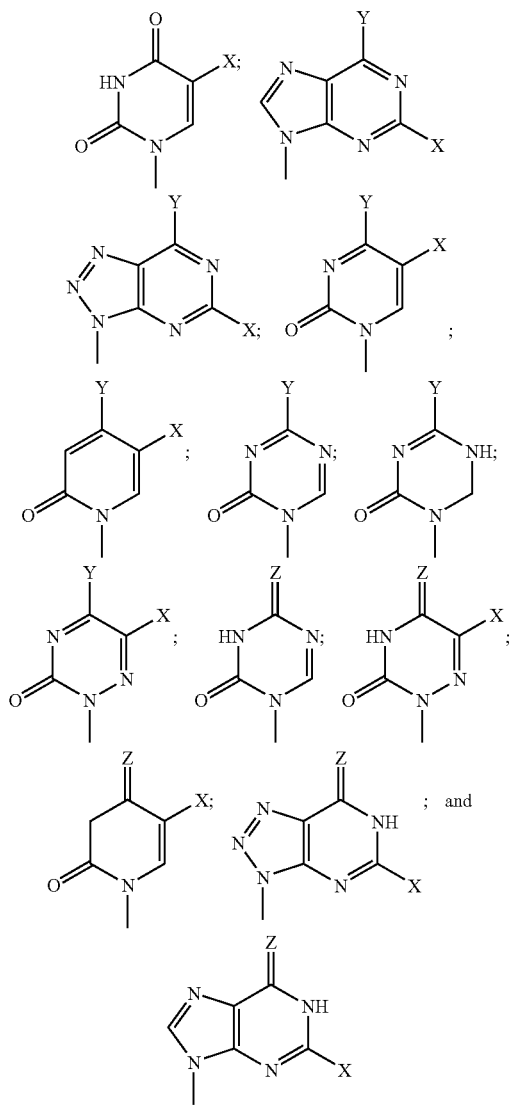

wherein Y is X, $N_3$, $NH_2$, monoalkylamino, or dialkylamino; Z is O or S; and X is selected from the group consisting of hydrogen, halo, hydroxy, alkoxy, alkyl, haloalkyl, alkenyl, haloalkenyl, alkynyl, amino, monoalkylamino, dialkylamino, thioaryl, thioalkyl, allylamino, cyano and nitro; tautomers thereof; and pharmaceutically acceptable salts thereof.

It has also been found according to the present invention that the above-disclosed compounds of formula 1 can be used to inhibit DNA replication in a mammalian cell by contacting the cell with at least one of these compounds.

The present invention also relates to pharmaceutical compositions containing the above disclosed compounds of formula 1 in amounts effective as anticancer or antiviral agents.

Furthermore, the present invention relates to treating a patient in need of an anticancer agent or antiviral agent by administering to the patient an anticancer or antiviral effective amount of a compound of formula 1.

The present invention also relates to preparing the above compounds. In particular, compounds of the present invention can be prepared as follows:

A. reacting a 2,3,5-tri-O-aryl or O-alkyl-D-arabinofuranoside with benzyl mercaptan in the presence of stannic chloride to produce the corresponding dithioacetal such as 2,3,5-tri-O-benzyl-D-arabinose dibenzyl dithioacetal;

B. subjecting the product from A to cyclization converting the D-arabino to the corresponding L-xylo compound such as 2,3,5-tri-O-benzyl dithio L-xylofuranoside;

C subjecting the product from B to acidolysis to form the corresponding O-acetyl-4-thio-L-xylofuranose such as 2,3,5-tri-O-benzyl-1-O-acetyl-4-thio-L-xylofuranose;

D. subjecting the product from C to reaction with dichloropurine to form the corresponding dichloropurine compound such as 9-(2,3,5-tri-O-benzyl-4-thio-α and β-L-xylofuranosyl)-2,6-dichloropurine;

E. subjecting the product from D to reaction with ammonia to produce the corresponding 2-chloroadenine nucleoside;

F. subjecting the product from E to removal of the O-aryl or O-alkyl group to form for example 2-chloro-9-(4-thio-α-L-xylofuranosyl)adenine; or 2-chloro-9-(4-thio-β-L-xylofuranosyl)adenine;

G. subjecting the product from D to reaction with an azide to form the corresponding diazide;

H. reducing the diazide from G to form the corresponding diamino purine compound; and I. optionally deblocking the diamino purine from H to form the corresponding diamino nucleoside; and J. optionally converting the diamino nucleoside from 1 to the corresponding guanine nucleoside; or K. coupling the product from B with thymine, uracil or cytosine or substituted analogs thereof; and L. optionally deblocking the coupled product from K to provide the corresponding nucleoside.

Still other objects and advantages of the present invention will become readily apparent by those skilled in the art from the following detailed description, wherein it is shown and described only the preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description contained herein is to be regarded as illustrative in nature and not as restrictive.

BEST AND VARIOUS MODES FOR CARRYING OUT INVENTION

The present invention relates to compounds represented by the formula 1:

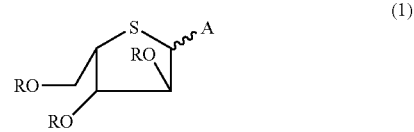

wherein each R individually is H, or an acyl group.

The compounds of the present invention include those wherein all three R groups are the same, or wherein at least one group differs from the others, or wherein all three differ including different acyl groups.

A is selected from the group consisting of:

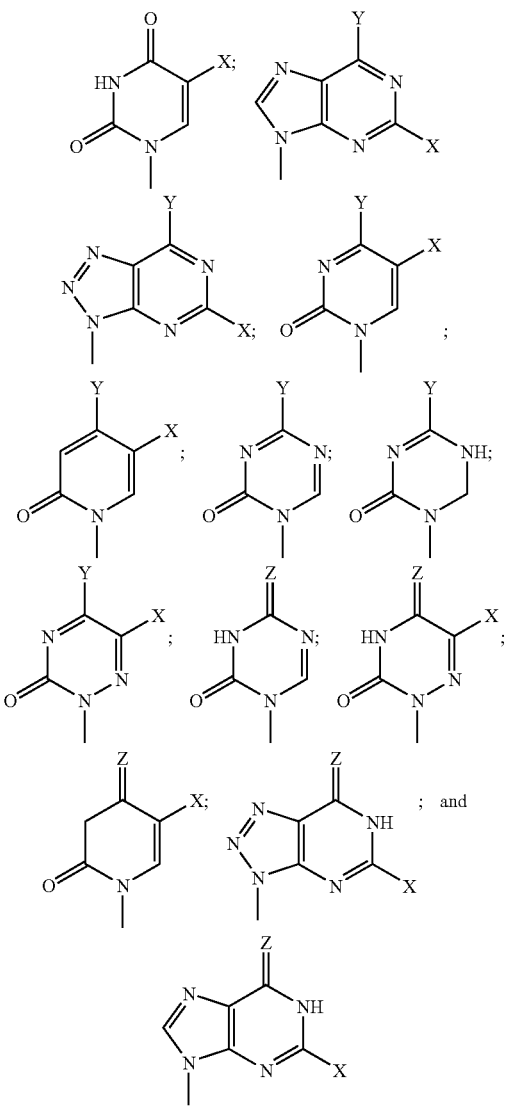

wherein Y is X, $N_3$, $NH_2$, monoalkylamino, or dialkylamino; Z is O or S, and X is selected from the group consisting of hydrogen, halo, hydroxy, alkoxy, alkyl, haloalkyl, alkenyl, haloalkenyl, alkynyl, amino, monoalkylamino, dialkylamino, thioaryl, thioalkyl, allylamino, cyano and nitro; tautomers thereof; and pharmaceutically acceptable salts thereof.

Suitable alkyl groups for X typically contain 1–6 carbon atoms and can be straight or branched chain. Some examples are methyl, ethyl, i-propyl, n-propyl, i-butyl, n-butyl, pentyl and hexyl.

Suitable acyl groups include acetyl, benzoyl and toluoyl.

Suitable halogen groups for X include Cl, Br and F.

Suitable alkoxy groups typically contain 1–6 carbon atoms and include methoxy, ethoxy, propoxy and butoxy.

Suitable haloalkyl groups typically contain 1–6 carbon atoms and can be straight or branched chain and include Cl, Br or F substituted alkyl groups including the above specifically disclosed alkyl groups.

Suitable alkenyl groups typically contain 2–6 carbon atoms and include ethenyl and propenyl.

Suitable haloalkenyl groups typically contain 1–6 carbon atoms and include Cl, Br or F substituted alkenyl groups including the above specifically disclosed alkenyl groups.

Suitable alkynyl groups typically contain 1–6 carbon atoms and include ethynyl and propynyl.

Suitable monoalkylamino groups for X contain 1–6 carbon atoms and include monomethylamino, monoethylamino, mono-isopropylamino, mono-n-propylamino, mono-isobutyl-amino, mono-n-butylamino, mono-n-hexylamino and monocyclopropylamino. The alkyl moiety can be straight or branched chain.

Suitable dialkylamino groups for Y and X contain 1–6 carbon atoms in each alkyl group. The alkyl groups can be the same or different and can be straight or branched chain. Examples of some suitable groups are dimethylamino, diethylamino, ethylmethylamino, dipropylamino, dibutylamino, dipentylamino, dihexylamino, methylpentylamino, ethylpropylamino and ethylhexylamino.

Preferred compounds according to the present invention include:
2-chloro-9-(4-thio-α-L-xylofuranosyl)adenine;
2-chloro-9-(4-thio-β-L-xylofuranosyl)adenine;
9-(2,3,5-tri-O-benzyl-4-thio-α,L-xylofuranonyl)-9H-purine-2,6-diamine;
9-(2,3,5-tri-O-benzyl-4-thio-β,L-xylofuranosyl-9H-purine-2,6-diamine;
9-(4-thio-α-L-xylofuranosyl)-9H-purine-2,6-diamine;
9-(4-thio-β-L-xylofuranosyl)-9H-purrine-2,6-diamine;
9-(4-thio-β-L-xylofuranosyl) guanine;
1-(2,3,5-tri-O-benzyl-4-thio-α,β-L-xylofuranosyl) thymine;
1-(2,3,5-tri-O-benzyl-4-thio-α,β-L-xylofuranosyl) uracil;
1-(4-thio-α,β-L-xylofuranosyl)thymine;
1-(4-thio-α,β-L-xylofuranosyl)uracil;
1-(2,3,5-tri-O-benzyl-4-thio-α,β-L-xylofuranosyl)cytosine; and
1-(4-thio-α,β-L-xylofuranosyl)cytosine.

Compounds of the present invention can be prepared by following the reaction schemes illustrated in Scheme A below and the specific examples which illustrate preparing preferred compounds of the present invention to facilitate an understanding of the present invention. For instance, methyl 2,3,5-tri-O-benzyl-D-arabinofuranoside (3) can be prepared by known two steps procedure starting with arabinose. Conversion to dibenzyl dithioacetal can be accomplished by employing benzyl mercaptan and stannic chloride. A 63% yield after chromatographic purification was achieved. Cyclization at C-4 involving a single inversion, thus converting the D-arabino to the L-xylo configuration, was accomplished employing triphenylphosphine, iodine, and imidazole in 72% yield. The final step, replacement of the benzylthio group at C-1 by an acetoxy group, involved treatment of 5 with mercuric acetate in acetic acid at room temperature. The overall yield of 6 from 1, including four column purifications, was 32%, and afforded a ca 1:1 mixture of α,β anomers.

A series of purine nucleoside analogs were prepared through the coupling of 6 and 2,6-dichloropurine. A Lewis acid catalyzed reaction utilizing stannic chloride in acetonitrile was found to be an efficient method to achieve this coupling, and 30 and 25% yields of α and β anomers of 7 were obtained after chromatographic purification/separation. After treatment with ethanolic ammonia to produce the respective blocked 2-chloroadenine nucleosides 8α and 8β, removal of the O-benzyl groups was accomplished with boron trichloride in dichloromethane at −50° C. to yield the nucleoside targets 9α and 9β. Treatment of 7α and 7β with sodium azide in 95% aqueous ethanol at reflux produced the corresponding 2,6-diazido intermediates 10α and 10β, which were subjected to reduction with stannous chloride in dichloromethane to afford the blocked diaminopurine nucleosides 11α and 11β in good yields. Deblocking of 11α and 11β with boron trichloride in dichloromethane produced the target diamino nucleoside 12α and 12β. The conversion of 12β to the corresponding guanine nucleoside 13 was accomplished by treatment with adenosine deaminase under standard conditions. Though the deamination was slow, it went to completion at room temperature in 72 hours. Cytosine, thymine and uracil were coupled with thiosugar 5 to afford 14α (31%), 14β (30%), 16αβ (60%) and 18αβ (70%) respectively, which were deblocked by boron trichloride to give the nucleosides 15α (70%), 15β (70%), 17αβ (65%) and 19αβ (65%) respectively.

The pharmaceutically acceptable effective dosage of the active compound of the present invention to be administered is dependent on the species of the warm-blooded animal (mammal), the body weight, age and individual condition, and on the form of administration.

The pharmaceutical composition may be oral, parenteral, suppository or other form which delivers the compounds used in the present invention into the bloodstream of a mammal to be treated.

The compounds of the present invention can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.001 to 1000 milligram (mg) per kilogram (kg) of body weight, with the preferred dose being 0.1 to about 30 mg/kg.

Dosage forms (compositions suitable for administration) typically contain from about 1 mg to about 100 mg of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms. The active ingredient can also be administered intranasally (nose drops) or by inhalation. Other dosage forms are potentially possible such as administration transdermally, via a patch mechanism or ointment.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company, a standard reference text in this field.

Useful pharmaceutical dosage forms for administration of the compounds according to the present invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate coatings may be applied to increase palatability or delay absorption.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited applications may provide further useful information, these cited materials are hereby incorporated by reference in their entirety.

The following non-limiting examples are presented to further illustrate the present invention. The NMR spectra reported in the examples below was determined by NOE difference spectroscopy.

EXAMPLE 1

Preparation of 2,3,5-Tri-O-benzyl-D-arabinose Dibenzyl Dithioacetal (4)

D-Arabinose (1, 25 g, 167 mmol) was stirred for 5 hours in 0.5% hydrogen chloride in methanol (675 mL) at room temperature and then neutralized with Amberlite IRA-400 OH anion exchange resin. The filtrate and washings were combined and evaporated to dryness and the crude product was purified by silica gel chromatography ($CHCl_3$/MeOH, 92:8) to afford 26.2 g of methyl D-arabinofuranoside (2, 95% yield) as an and (1:1) mixture. MS 164 $(M)^+$.

To an ice-cold solution of 2 (10 g, 60.9 mmol) in dry tetrahydrofuran (350 mL) was added sodium hydride (60% dispersion in mineral oil, 14.8 g, 370 mmol) and the reaction mixture was stirred for 15 min under $N_2$. To this reaction mixture was added solid tetrabutylammonium iodide (0.36 g, 0.96 mmol) followed by a dropwise addition of benzyl bromide (36.6 g, 214 mmol). The reaction mixture was stirred for 3 days at room temperature. After the addition of methanol (25 mL), the solution was evaporated under reduced pressure, and the crude product was purified by silica gel chromatography (cyclohexane/EtOAc, 9:1) to afford pure methyl 2,3,5-tri-O-benzyl-D-arabinofuranoside (3, 23 g, 87% yield). MS 435 $(M+H)^+$.

To a solution of 3 (42 g, 97 mmol) in dichloromethane (1000 mL) were added benzyl mercaptan (49.6 g, 400 mmol) and stannic chloride (4.93 g, 18.9 mmol), and the reaction mixture was stirred at room temperature overnight. After neutralization with 5% aqueous $NaHCO_3$ (750 mL), the organic layer was separated and the aqueous layer was extracted with dichloromethane (500 mL). The combined organic layers were evaporated, and crude 4 was purified by silica gel chromatography (cyclohexane/EtOAc, 99:1) to afford 4 (8.53 g, 63%) of sufficient purity to carry forward. MS 657 $(M+Li)^+$.

EXAMPLE 2

Preparation of 2,3,5-Tri-O-benzyl-1-O-acetyl-4-thio-L-xylofuranose (6)

To a solution of 4 (13.0 g, 20 mmol) in dry 2:1 toluene/acetonitrile (200 mL) were added triphenylphosphine (15.7 g, 60 mmol), iodine (12.7 g, 50 mmol) and imidazole (5.44 g, 80 mmol). The reaction mixture was stirred at 90° C. for 24 hours after which time the solution was evaporated to dryness. The crude product was purified by silica gel chromatography (cyclohexane/EtOAc, 4:1) to afford benzyl 2,3,5-tri-O-benzyl-1,4-dithio-L-Xylofuranoside as a syrup (5, 9.0 g, 72%). MS 543 $(M+H)^+$.

To a suspension of mercuric acetate (7.29 g, 22.9 mmol) in acetic acid (96 g) was added 5 (5.42 g, 10 mmol), and the resulting mixture was stirred at room temperature for 2 h. The reaction mixture was diluted with dichloromethane (200 mL) and washed successively with water, saturated aqueous NaHCO$_3$ and 5% aqueous KCN solution. The organic layer was dried over Na$_2$SO$_4$ and concentrated. Chromatography of the crude product using cyclohexane:ethylacetate (98:2) as eluent gave a mixture of and (1:1) anomers of 6 (3.73 g, 78%) as a colorless syrup. MS 479 (M+H)$^+$.

EXAMPLE 3

Preparation of 9-(2,3,5-Tri-O-benzyl-4-thio-α and -β-L-xylofuranosyl)-2,6-dichloropurine (7α and 7β)

To a stirred mixture of 6 (0.956 g, 2 mmol) and 2,6-dichloropurine (0.568 g, 3 mmol) in acetonitrile (50 mL) at room temperature was added a solution of stannic chloride in dichloromethane (3 mL of 1.0 M) over 1 min and stirring was continued for 2 hours. The reaction mixture was quenched by pouring it into a mixture of 50 mL of dichloromethane and 25 mL of saturated NaHCO$_3$. The organic phase was dried (MgSO$_4$) and concentrated. The residue was purified by silica gel chromatography (cyclohexane/EtOAc, 9:1) to afford 7α (364 mg, 30%) eluting first followed by 7β (291 mg, 25%).
Compound 7α: MS 608 (M+H)$^+$.
Compound 7β: MS 608 (M+H)$^+$.

EXAMPLE 4

Preparation of 2-Chloro-9-(4-thio-α-L-xylofuranosyl)adenine (9α)

A mixture of compound 7α (608 mg, 1 mmol) and saturated ethanolic ammonia (100 mL) was heated at 50° C. in a glass-lined stainless steel pressure vessel for 48 hours. The reaction mixture was evaporated to dryness to afford a solid (8α) that was dissolved in dichloromethane (50 mL) and was added dropwise to a solution of 1 M BCl$_3$ in CH$_2$Cl$_2$ (100 mL) at −50° C. Solid precipitated from the solution near the end of addition. The reaction in a tightly sealed flask was stored at −20° C. for 16 h. The resulting clear solution was evaporated to dryness at −20° C. to give a dark residue. A solution of this material in ice-cold CH$_2$Cl$_2$ (25 mL) was evaporated to dryness four times to provide a foam. Ice-cold saturated aqueous NaHCO$_3$ (20 mL) was added to the foam, and the mixture was stirred vigorously until the pH remained stable (pH 7–8). Water (150 mL) was added to form a clear solution that was extracted with two portions of CH$_2$Cl$_2$ (50 mL, 25 mL) to remove color and impurities. The colorless aqueous layer was held briefly under vacuum to remove residual CH$_2$Cl$_2$ before being applied to a column (13×190 mm) of Bio Beads SM-4 (100–200 mesh) equilibrated in water. Water elution with fractions monitored at 254 nm provided pure 9α (175 mg, 55%); TLC, 3:1:0.1 CHCl$_3$-MeOH—NH$_4$OH, R$_f$ 0.55; m.p. 140 MS 318 (M+H)$^+$.

EXAMPLE 5

Preparation of 2-Chloro-9-(4-thio-β-L-xylofuranosyl)adenine (9β)

The compound of this example was prepared from 7 by the same procedure as reported for 9β in 45% yield; TLC, 3:1:0.1 CHCl$_3$-MeOH—NH$_4$OH, R$_f$ 0.45; m p 235: MS 318 (M+H)$^+$.

EXAMPLE 6

Preparation of 9-(2,3,5-Tri-O-benzyl-4-thio-α-L-Xylofuranosyl)-9H-purine-2,6-diamine (11)

A solution of 7α (303 mg, 0.5 mmol) and sodium azide (162.5 mg, 2.5 mmol) in 20 mL of 95% ethanol was heated at reflux for 2 hours. The solvent was removed in vacuo, and the residue was partitioned between dichloromethane and water. The organic phase was dried (MgSO$_4$) and concentrated in vacuo to yield 290 mg of a yellowish solid (10α) [TLC: CHCl$_3$/MeOH, 97:3; Rf 0.45; mass spectrum, m/z 621 (M+H)$^+$], which was redissolved in 20 mL of dichloromethane and 2 mL of methanol. This solution was treated with stannous chloride (190 mg, 1 mmol) and the resulting suspension was stirred for 30 min. After evaporation of solvent, purification was accomplished by silica gel chromatography (CHCl$_3$/MeOH, 97:3) to afford 11α (214 mg, 75%), which was suitable for deblocking. MS 569 (M+H)$^+$

EXAMPLE 7

Preparation of 9-(2,3,5-Tri-O-benzyl-4-thio-β-L-Xylofuranosyl)-9H-purine-2,6-diamine (11β)

The compound of this example was prepared in 78% yield by the same procedure as reported above for 11α but starting from 7β, affording material suitable for deblocking. MS 569 (M+H)$^+$.

EXAMPLE 8

Preparation of 9-(4-Thio-α-L-Xylofuranosyl)-9H-purine-2,6-diamine (12α)

An ice-cold solution of 11α (218 mg, 0.38 mmol) in CH$_2$Cl$_2$ (2.6 mL) was added dropwise to a solution of 1 M BCl$_3$ in CH$_2$Cl$_2$ (30 mL) at −50° C. Solid precipitated from the solution near the end of addition. The reaction in a tightly sealed flask was stored at −20° C. for 16 hours. The resulting clear solution was evaporated to dryness at −20° C. to give a dark residue. A solution of this material in ice-cold CH$_2$Cl$_2$ (25 mL) was evaporated to dryness four times to provide a foam. Ice-cold saturated aqueous NaHCO$_3$ (20 mL) was added to the foam, and the mixture was stirred vigorously until the pH remained stable (pH 7–8). Water (150 mL) was added to form a clear solution that was extracted with two portions of CH$_2$Cl$_2$ (50 mL, 25 mL) to remove color and impurities. The colorless aqueous layer was held briefly under vacuum to remove residual CH$_2$Cl$_2$ before being applied to a column (13×190 mm) of Bio Beads SM-4 (100–200 mesh) equilibrated in water. Water elution with fractions monitored at 254 nm provided pure 12α that was crystallized from hot MeOH (81 mg, 71%). TLC, 3:1:0.1 CHCl$_3$-MeOH—NH$_4$OH, R$_f$ 0.48; m.p. 140; MS 299 (M+H)$^+$.

EXAMPLE 9

Preparation of 9-(4-Thio-β-L-Xylofuranosyl)-9H-purine-2,6-diamine (12β)

The compound of this example was prepared in 75% yield (Crystallized from water) by the same procedure as reported above for 12α but starting from 11β. TLC, 3:1:0.1 CHCl$_3$-MeOH—NH$_4$OH, R$_f$ 0.43 M.p 130; MS 299 (M+H)$^+$.

EXAMPLE 10

Preparation of 9-(4-Thio-β-L-xylofuranosyl)guanine (13)

To a solution of 12β (50 mg, 0.17 mmol) in 20 mL of water was added 100 units of adenosine deaminase type VIII (40 μL). The reaction was stirred for 72 hours, the solution was boiled for 3 min to deactivate the enzyme, and the suspension was treated with charcoal and filtered through Celite. The filtrate was concentrated to give gelatinous 13 which was dissolved in hot water (4 mL) and filtered through 0.45 μm filter (25 mm, Gelman Acrodisc GHP-GF). The clear filtrate was lyophilized to provide 13 as a fluffy white solid which was crystallized from water (20 mg, 40%): TLC, 3:1:0.1 CHCl$_3$-MeOH—NH$_4$OH, R$_f$ 0.40; m.p. 260; MS 300 (M+H)$^+$.

EXAMPLE 11

Preparation of 1-(2,3,5-Tri-O-benzyl-4-thio-L-Xylo-furanosyl)cytosine (14α and 14β)

To a suspension of cytosine (1.27 g, 11.5 mM) in anhydrous acetonitrile (30 mL) was added BSA (5.48 g, 27 mM). The resulting mixture was heated at 50° C. for 3 hours.

The mixture was cooled to room temperature and sugar 5 (2.53 g, 4.67 mM) was added followed by powdered 4A molecular seives (1.5 g) and NBS (1.78 mg, 10 mM). The suspension was heated at reflux for 50° C. 18 hours and then cooled to room temperature and filtered. Filtrate and washings were evaporated to dryness and purified by silica gel column (Chloroform and Ethylacetate 90:10) to afford 0.76 g (31%) of compound 14α and 0.75 g (30%) of 14β.
14α MS 530 (M+H)$^+$.
14β MS 530 (M+H)$^+$.

EXAMPLE 12

Preparation of 1-(2,3,5-Tri-O-benzyl-4-thio-α,β-L-Xylofuranosyl)thymine (16α,β)

To a suspension of thymine (2.0 g, 15.8 mM) in anhydrous acetonitrile (40 mL) was added BSA (8.23 g, 40.4 mM). The resulting mixture was heated at 50° C. for 3 hours. The mixture was cooled to room temperature and sugar 5 (7.48 g, 13.8 mM) was added followed by powdered 4A molecular seives (1.8 g) and NBS (2.66 g, 15 mM). The suspension was heated at reflux for 50° C. 18 hours and then cooled to room temperature and filtered. Filtrate and washings were evaporated to dryness and purified by silica gel column (Chloroform and Ethylacetate 90:10) to afford 4.51 g (60%) of compound 16 as 1:1α,β mixture (1:0.85). MS 545 (M+H)$^+$.

EXAMPLE 13

Preparation of 1-(2,3,5-Tri-O-benzyl-4-thio-α,β-L-Xylofuranosyl)uracil (18α,β)

To a suspension of Uracil (1.29 g, 11.5 mM) in anhydrous acetonitrile (30 mL) was added BSA (5.48 g, 27 mM). The resulting mixture was heated at 50° C. for 3 hours. The mixture was cooled to room temperature and sugar 5 (2.53 g, 4.67 mM) was added followed by powdered 4A molecular seives (1.5 g) and NBS (1.78 mg, 10 mM). The suspension was heated at reflux for 50° C. 18 hours and then cooled to room temperature and filtered. Filtrate and washings were evaporated to dryness and purified by silica gel column (Chloroform and Ethylacetate 90:10) to afford 10.73 g (70%) of compound 16 as mixture (1:1). MS 531 (M+H)$^+$.

EXAMPLE 14

Preparation of 1-(4-thio-α-L-Xylofuranosyl)cytosine (15α);

1-(4-thio-β-L-Xylofuranosyl)cytosine (15β);

1-(4-thio-α,β-L-Xylofuranosyl)thymine (17α,β);

1-(4-thioα,β-L-Xylofuranosyl)uracil (19β)

Compounds 14α, 14β, 16α,β and 18α,β were deblocked as disclosed above for 12 to afford compound 15α (70%) and 15β (70%); MS 259 (M+H)$^+$); 17α,β, (65% yield, MS 274 (M+H)$^+$); and 19α,β, (65% yield, MS 260(M+H) respectively.

Biological Data

The cell culture cytotoxicity of compounds of the present invention was determined against several different human cancel cell lines (see Table 1 below) and for antiviral activity (see Table 2 below).

TABLE 1

| | Cytotoxicity data: IC50(μM) | | | | | |
|---|---|---|---|---|---|---|
| compound | CCRF-CEM (leukemia) | CAKI-1 (renal) | DLD-1 (colon) | NCI-H23 (lung) | SK-MEL-28 (melanoma) | SNB-7 (CNS) |
| 9α | >100 | >100 | >100 | >100 | >100 | >100 |
| 9β | >100 | >100 | >100 | >100 | >100 | >100 |
| 12α | >100 | >100 | >100 | >100 | >100 | >100 |
| 12β | >100 | >100 | >100 | >100 | >100 | >100 |
| 13 | >100 | >100 | >100 | >100 | >100 | >100 |
| 15α | 8.0 | >100 | >100 | >100 | >100 | >100 |
| 15β | 11.0 | >100 | >100 | >100 | >100 | 90 |
| 17αβ | >100 | >100 | >100 | >100 | >100 | >100 |
| 19αβ | >100 | >100 | >100 | >100 | >100 | >100 |

TABLE 2

| | Antiviral (CMV) data | | |
|---|---|---|---|
| compound | IC50 | TC50 | TI |
| Ganciclovir | 8.6 μM | >10 μM | >11.6 |
| 12α | 0.051 μM | >10 μM | >196.1 |
| 15β | 0.022 μM | >10 μM | >454.5 |
| 15α | 0.026 μM | >10 μM | >384.6 |

IC 50: 50% Inhibitory Concentration of CMV
TC 50: Toxic Concentration at 50% cell viability
TI: Therapeutic Index (TC50/IC50)

What is claimed is:

1. Compound represented by the formula 1:

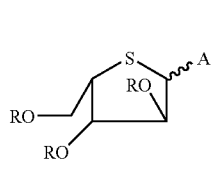 (1)

wherein each R individually is H, or an acyl group;
A is selected from the group consisting of

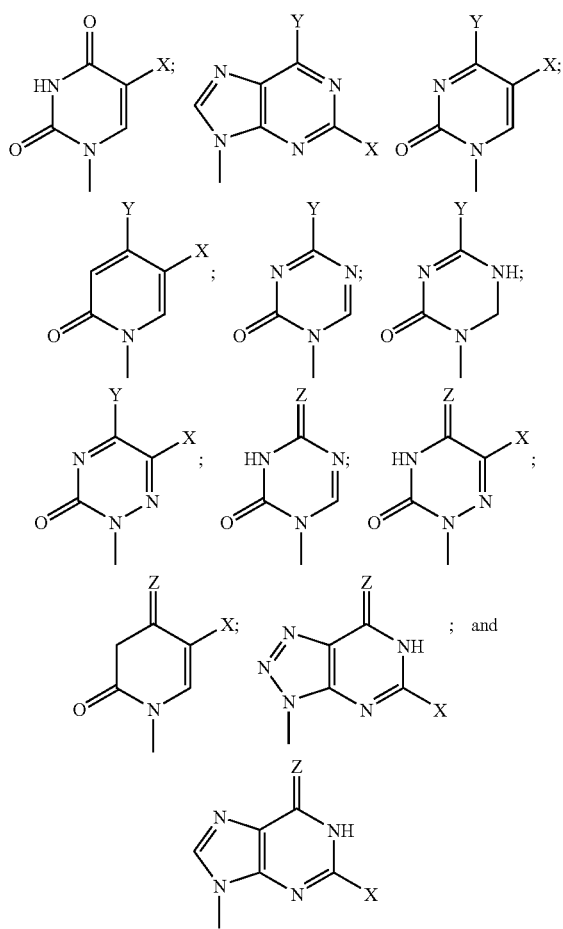

wherein Y is X, Z is O or S; and
X is selected from the group consisting of hydrogen, halo, hydroxy, alkoxy, alkyl, haloalkyl, alkenyl, haloalkenyl, alkynyl, amino, monoalkylaxnino, dialkylamino, thioaryl, thioalkyl, allylamino, cyano and nilro; tautomers thereof; and pharmaceutically acceptable salts thereof, and wherein said compound is in the L-xylo configuration.

2. The compound of claim 1 wherein X is chlorine.
3. The compound of claim 1 wherein X is $NH_2$.
4. The compound of claim 1 wherein X is H.
5. The compound of claim 1 wherein X is $CH_3$.
6. The compound of claim 1 wherein R is H.
7. The compound of claim 1 wherein R is benzoyl.

8. The compound of claim 1 wherein A is

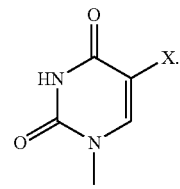

9. The compound of claim 1 wherein A is

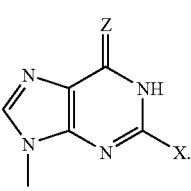

10. The compound of claim 1 being 9-(4-thio-β-L-xylofuranosyl) guanine.
11. A pharmaceutical composition comprising a conmpound according to claim 1 in an amount effective as an anticancer agent and a pharmaceuticel carrier.
12. A pharmaceutical composition comprising a compound according to claim 1 in an amount effective as an antiviral agent and a pharmaceutical carrier.
13. The compound of claim 1 wherein A is

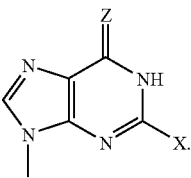

14. A pharmaceutical composition comprising a compound according to claim 1 in an amount effective as an antiviral agent and a pharmaceutical carrier.

15. Compound represented by the formula 1:

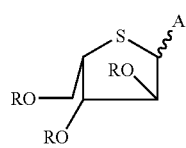 (1)

wherein each R individimlly is H, or an acyl group;
A is selected from the group consisting of

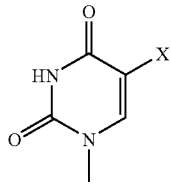 and 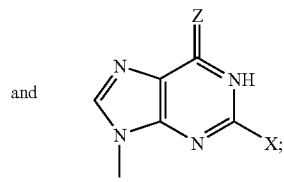

and wherein Y is X, $N_3$, $NH_2$, monoalkylamino or dialkyiamino; Z is O or S; and X is selected from the group consisling of hydrogen, halo, hydroxy, alkoxy, alkyl, haloalkyl, alkenyl, haloalkenyl, alkynyl, amino, monoalkylamino, dialkylamino, thioaryl, thioalkyl, allylamino, cyano and nitro; tautomers thereof; and pharmaceutically acceptable salts thereof, and wherein said compound is in the L-xylo configuration.

16. The compound of claim 15 wherein Y is $NH_2$.

17. The compound of claim 15 wherein R is H.

18. The compound of claim 15 wherein R is benzoyl.

19. The compound of claim 15 being 1-(4-thio-α,β-L-xylofuranosyl)cytosine.

20. The compound of claim 15 being 1-(2,3,5-tri-O-benzyl-4-thio-α,β-L-xylofuranosyl)cytosine.

21. The compound of claim 15 being 1-(4-thio-α,β-L-xylofuranosyl)uracil.

22. The compound of claim 15 being 1-(4-thio-α,β-L-xylofuranosyl)thymine.

23. The compound of claim 15 being 1-(2,3,5-tri-O-benzyl-4-thio-α,β-L-xylofuranosyl) uracil.

24. The compound of claim 15 being 1-(2,3,5-tri-O-benzyl-4-thio-α,β-L-xylofuranosyl) thymine.

25. The compound of claim 15 being 9-(4-thio-α-L-xylofuranosyl)-9H-purine-2,6-diamine.

26. The compound of claim 15 being 9-(2,3,5-thio-O-benzyl-4-thio-α, L-xylofuranosyl)-9H-purine-2,6-diamine.

27. The compound of claim 15 wherein A is

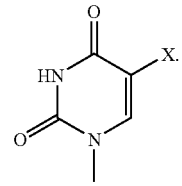

28. A pharmaceutical composition comprising a compound according to claim 15 in an amount effective as an anticancer agent and a pharmaceutical carrier.

* * * * *